United States Patent [19]

Salmond

[11] 4,058,538
[45] Nov. 15, 1977

[54] 3α,5α-CYCLO-6β-ALKOXY-α²²-BIS-NOR CHOLESTENE DERIVATIVES

[75] Inventor: William G. Salmond, Kalamazoo, Mich.

[73] Assignee: The Upjohn Company, Kalamazoo, Mich.

[21] Appl. No.: 708,821

[22] Filed: July 26, 1976

Related U.S. Application Data

[63] Continuation-in-part of Ser. No. 544,174, Jan. 27, 1975, Pat. No. 3,994,934.

[51] Int. Cl.² ............................................. C07J 5/00
[52] U.S. Cl. ................................................. 260/397.2
[58] Field of Search ..................................... 260/397.2

[56] References Cited

U.S. PATENT DOCUMENTS 3,993,675  11/1976  Uskokovic et al. ............... 260/397.2
3,994,934  11/1976  Salmond .............................. 260/397.2

*Primary Examiner*—Elbert L. Roberts
*Attorney, Agent, or Firm*—Martin B. Barancik

[57] ABSTRACT

3α,5α-cyclo-6β-alkoxy-Δ²²-25-hydroxy, oxy and acyloxy bisnorcholestane and analogues.

4 Claims, No Drawings

3α,5α-CYCLO-6β-ALKOXY-α²²-BIS-NOR CHOLESTENE DERIVATIVES

CROSS REFERENCE TO RELATED APPLICATIONS

This application is a continuation-in-part of my co-pending application Ser. No. 544,174 filed Jan. 27, 1975, now U.S. Pat. No. 3,994,934.

BRIEF DESCRIPTION OF THE INVENTION

A new method for synthesizing 3α,5α-cyclo-6β-alkoxy-25-hydroxy and acyloxy sterol derivatives has been discovered. These sterols are intermediates in the production of 25-hydroxy cholesterol derivatives and thence 25-hydroxy Vitamin D metabolites and their analogues.

This new method comprises stereospecifically reacting an ylide

Formula I

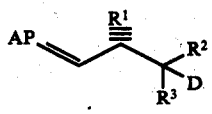

wherein A is the portion of a Wittig reagent inert to the reaction medium, and $R^1$, $R^2$ and $R^3$ are each selected from hydrogen and methyl and D is selected from the group consisting of $O^-$ and

$OCR^4$ wherein $R^4$ is selected from the group consisting of alkyl of one to six carbon atoms, phenyl, benzyl, and phenethyl, with 3α,5α-cyclo-6β-alkoxybisnorcholanaldehyde, alkoxy of one to six carbons atoms, inclusive, to form compounds Formula II

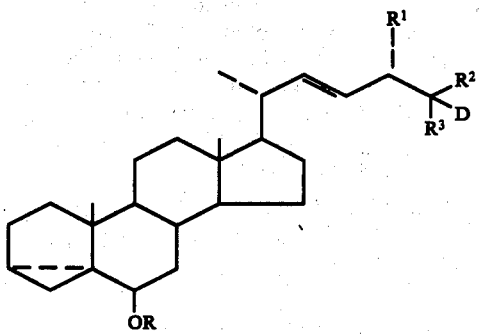

wherein R is alkyl of one to six carbon atoms, inclusive, and $R^1$, $R^2$, $R^3$ and D are defined as above.

A further aspect of the invention is the preparation of a betaine which comprises reacting the methylene phosphorane

 Formula III wherein A is the portion of a Wittig reagent inert to the reaction medium, with the epoxide Formula IV

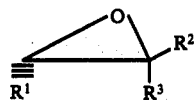

wherein $R^1$, $R^2$ and $R^3$ are each selected from hydrogen and methyl to form Formula V

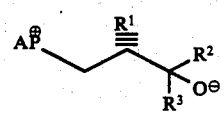

Further aspects of the invention are novel cholestanes and i-ethers.

DETAILED DESCRIPTION OF THE INVENTION

The phrase "alkyl of one to six carbon atoms, inclusive" covers methyl, ethyl, propyl, butyl, pentyl, hexyl and isomers thereof. Examples of isomers are isopropyl, tert.-butyl, neopentyl and 2,3-dimethylbutyl The betaine of Formula V is prepared from the reaction of a methylenephosphorane, Formula III, with an epoxide of Formula IV. The A group of the phosphorane is a group commonly employed in a Wittig reagent, see, for example, Tripett, Quart. Rev. XVII, No. 4, p. 406 (1963), and House, "Modern Synthetic Reactions" second edition, p. 682-709. Additionally, the group should be substantially inert with respect to the reaction medium. Examples of such groups include triphenyl, triphenyl substituted with one to three alkyl groups on each phenyl, each alkyl being the same or different and having from one to four carbon atoms, inclusive. Additionally, A can be a monosubstituted phenyl with two unsubstituted phenyls, for example, (phenyl)₂, p-carboxyphenyl. Other phosphoranes which can be used include the dimethylaminoethylenephosphorane, that is $(Me_2N)_3P=CH_2$.

The phosphorane and the epoxide are reacted at room temperature or any convenient temperature of from about 0° to about 40° C. although higher or lower temperature can be employed at times. An inert organic solvent is used as well. See Tripett and House, supra, for suitable solvents. Examples of such solvents include tetrahydrofuran, diethyl ether, hexane, pentane, benzene, heptane, octane, toluene, and dioxane.

Once the betaine is prepared, it is converted to the ylide, Formula I, by conventional reagents and conditions, for example, by contact with a strong base. Illustrative of the reagents which can be employed to convert to betaine to the ylide are the organo-lithium reagents, such as the alkyl lithium reagents of one to four carbon atoms, sodamide, sodium hydride, lithium amides and so forth. Art-recognized conditions are used for this reaction. The preferred reagent is n-butyl lithium.

The ylide of Formula I where D is $O^-$ is then contacted with the 3α,5α-cyclo-6β-alkoxybisnor-cholanaldehyde to form a compound of Formula II wherein D is $O^-$. The temperature at which this reaction occurs is not unduly significant. Temperature of from about 0° to about 40° C. can be employed. The preferred temperature range is from about 15° to about 25° C. It should be noted that the cation is the metal portion of the base employed to convert the betaine to the ylide.

To prepare compounds of Formula I where D is

OCR$^4$, the betaine of Formula V is acylated with the desired R$^4$ acylating agent. For example, and R$^4$ acid anhydride, or and R$^4$ acyl halide, preferably chloride, are readily employed at standard reaction conditions. The resulting salt is then reacted with a strong base such as lithium diisopropylamide to form the ylide of Formula I (Dacyloxy). This is then reacted with the bisnorcholanaldehyde to form a compound of Formula II wherein D is

OCR$^4$.

Alternatively, these compounds of Formula II wherein D is

OCR$^4$ are prepared by reacting the ylide wherein D is O− with the bisnorcholanaldehyde and then reacting the resulting 25-oxyanionic steroid with an acylating agent similar to that used earlier, thereby forming the i ether with D as

OCR$^4$.

The above i-ethers can be readily converted to 25-hydroxy-cholesterol and thence to 25-hydroxycholecalciferol.

After compounds of Formula II are prepared, the double bond between C$^{22}$ and C$^{23}$ can be saturated by conventional means thereby preparing the intermediate to 25-hydroxy Vitamin D$_3$ and analogues, see Formula VI.

Formula VI

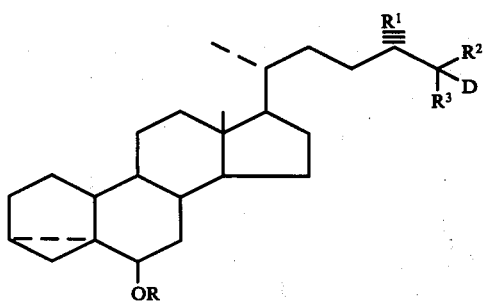

R, R$^1$, R$^2$, R$^3$, and D defined as above.

A suitable saturation method is catalytic hydrogenation. The hydrogenation is carried out with a noble metal catalyst in a suitable inert organic solvent at appropriate pressures. Platinum or palladium are preferred noble metals. Inert organic solvents such as ethyl acetate, methylene chloride and tetrahydrofuran can be employed. Ethyl acetate is preferred. Any hydrogenation pressure which brings about a reasonable rate of reaction can be used. Pressures as low as 15 psi can be employed. The upper limit of pressure is dependent upon the loss of yield from the opening of the cyclopropane ring. Pressure up to about 100 psi or even higher can be employed with facility.

Following are examples illustrative of the invention scope. These examples are meant to exemplify and not to narrow the invention.

EXAMPLE 1

3α, 5α-cyclo-6β-methoxy-25-hydroxy-26,27-bisnorcholest-22-ene

Methyltriphenylphosphonium bromide (17.9 g) is stirred under nitrogen in 150 ml. tetrahydrofuran containing 15 ml. hexamethylphosphoric triamide. n-Butyl lithium (35 ml. of a 1.5M solution in hexane) is added dropwise to yield a bright red solution. This solution is left for 30 minutes before ethylene oxide (ca. 5.0 g.) is added. The reaction vessel is then sealed and the temperature raised to 35° C. for 1 hour. After this time the nitrogen inlet is replaced and the reaction vessel purged with nitrogen to remove the excess ethylene oxide. At this point the reaction mixture is pale yellow. A further 35 ml. of n-butyl lithium is added. This causes a bright red color to be formed, and as the addition continues the temperature rises to 35° C. Fifteen minutes after the addition is completed, a solution of 3α,5α-cyclo-6β-methoxybisnorcholanaldehyde (17.0 g. in 150 ml. hexane) is added dropwise until all the color of the ylide is removed. The reaction mixture is then quenched with water and extracted with ethyl acetate. The residue after evaporation and chromatography on neutral alumina gives the desired product as plates recrystallized from acetonitrile, m.p. 104°–105° C.

NMR (CDCl$_3$): 0.3–0.67m; 0.73s (3H); 1.01s (3H); 1.01d, J=6Hz, (3H); 2.77 b.t. (1H); 3.30s (3H); 3.60 t, J-6Hz (2H); 5.37m (2H). R$_f$: (5% CH$_3$OH/CHCl$_3$) 0.58.

EXAMPLE 2

3α,5α-cyclo-6β-methoxy-25-hydroxy-26,27-bisnorcholestane

The Δ$^{22}$ compound (2.0 g.) obtained from Example 1 is dissolved in 40 ml. methylene chloride. 5% Platinum on carbon catalyst (0.5 g.) is added and the mixture hydrogenated at 90 psi for 2 hours. The catalyst is filtered off and evaporation of the filtrate yields a crystalline residue, recrystallized from acetonitrile by displacement of methylene chloride to give needles, m.p. 128°–129° C.

NMR (CDCL$_3$): 0.3–0.67m; 0.73s (3H); 1.01s (3H); 2.77 b.t. (1H); 3.30s (3H); 3.60 t, J=6Hz, (2H). R$_f$: (5% CH$_3$OH/CHCl$_3$) 0.52.

EXAMPLE 3

3α,5α-cyclo-6β-methoxy-Δ$^{22}$-25-acetoxy, 26,27-bisnorcholestane

To a stirred suspension of methyltriphenylphosphonium bromide (3.57 g.) in dry tetrahydrofuran (30 ml.) is added at room temperature and under a blanket of nitrogen a solution of n-butyl lithium in hexane (15%, 6.3 ml.). Stirring is continued for 30 minutes and then excess isobutylene oxide added. After 1 hour the flask is purged with a stream of nitrogen to remove the excess oxide and then one molar proportion of acetic anhydride is added. After 15 minutes a solution of lithium diisopropylamide in hexane, prepared from 6.3 ml. of a 15% solution of n-butyl lithium in hexane and 1.1 g. diisopropylamine in 10 ml. hexane, is added, followed thirty minutes later by a solution of 3.4 g. of the bisnorcholanaldehyde in 25 ml. hexane. After yet a further thirty minutes the mixture is poured into methanol and worked up as in Example 1 to yield the 3α, 5α-cyclo-6β-methoxy-25-acetoxy, 26,27-bisnorcholest-22-ene.

EXAMPLE 4

3α,5α-cyclo-6β-methoxy-25-acetoxy-cholest-22-ene

To a stirred suspension of methyltriphenylphosphonium bromide (3.57 g.) in dry tetrahydrofuran (30 ml.) is added at room temperature and under a blanket of nitrogen a solution of n-butyl lithium in hexane (15%, 6.3 ml.). Stirring is continued for 30 minutes and then excess of isobutylene oxide is added. After 1 hour the flask is purged with a stream of nitrogen to remove the excess oxide and then a further 6.3 ml. of the n-butyl lithium solution added. After 30 minutes a solution of bisnorcholanaldehyde in hexane (3.40 g. in 30 ml.) is added. After a further 15 minutes, 1.4 ml. acetic anhydride is added. After yet a further 30 minutes the mixture is poured into methanol, and Skellysolve B (ca 200 ml.) is added followed by ca. 20 ml. water. This causes two layers to form, the lower layer containing predominantly the by-product triphenyl phosphine oxide, and the upper layer containing the desired 25-acetate. Drying of the upper layer followed by evaporation yields a residue of the desired 3α,5α-cyclo-6β-methoxy-25-acetoxy-cholest-22-ene.

NMR (CDCl$_3$): δ0.75s (3H); 1.03s (3H); 1.40s (6H); 1.93s (3H); 2.77m (1H); 3.20s (3H); 5.30m (2H).

EXAMPLE 5

3α,5α-cyclo-6β-methoxy-25-benzoxy-cholest-22-ene

In a fashion directly analogous to that described in Example 4 but replacing the acetic anhydride by benzoyl chloride, there is obtained the compound 3α, 5α-cyclo-6β-methoxy-25-benzoxy-cholest-22-ene.

The 66 $^{22E}$ compound has the NMR (CDCl$_3$): δ0.27–0.70m (3H); 0.70s (3H); 0.97d, J=6Hz, (3H); 1.02s (3H); 1.55s (6H); 2.50–2.67m (1H); 2.77t (1H); 3.30s (3H); 5.20–5.50m (2H); 7.23–7.63m (3H); 7.87–8.17m (2H).

The Δ$^{22E}$ compound has the NMR (CDCl$_3$): δ0.27–0.73m (3H); 0.78s (3H); 0.97d, J=6, (3H); 1.03s (3H); 1.58s (6H); 2.67–2.87m (2H); 3.32s (3H); 5.2–5.47m (2H); 7.2–7.58m (3H); 7.88–8.13m (2H).

EXAMPLE 6

In an analogous manner to Examples 1 through 5 the following illustrative compounds can be prepared.

| | |
|---|---|
| 1) R$^1$=H, R$^2$=R$^3$=CH$_3$ | precursor to the compound claimed in U.S.P. 3,786,062 |
| 2) R$^1$=R$^2$=R$^3$=CH$_3$ | precursors to 25-OH-D$_2$ derivatives |
| 3) R$^1$=H, R$^2$=R$^3$=CH$_3$ | precursor to 25-HCC |

EXAMPLE 7

In a manner similar to Examples 1 through 6, compounds where R is illustratively ethyl, propyl, butyl, pentyl, hexyl, isopropyl, tert.butyl, neopentyl, and 2,3-dimethylbutyl are prepared where R$^1$, R$^2$, and R$^3$ are each hydrogen or methyl.

EXAMPLE 8

In a similar manner to Examples 1 through 7, compounds where R is propionoxy, tert.butoxy, hexoxy, phenylacetoxy, and 2' phenylpropionoxy are readily prepared.

It should be noted that the compounds of Formula II wherein D is O− can be quenched in an aqueous medium such as water or by ordinary work-up procedures to produce the compounds of Formula II wherein D is hydroxy. These compounds can also be easily saturated to form the i-ether derivatives of 25-hydroxycholesterol and its analogues.

Following is an example of the production of a compound of Formula II wherein D is hydroxy, R$^1$ is hydrogen and R$^2$ and R$^3$ are methyl.

EXAMPLE 9

3α,5α-cyclo-6β-methoxy-25-hydroxy-cholest-22-ene

The procedure of Example 4 for preparing the ylide and contacting the ylide with the aldehyde is followed. However, instead of quenching with acetic anhydride, the reaction mixture of aldehyde and ylide is quenched with water and then the mixture is extracted with ethyl acetate. The extracts are washed with water, dried and evaporated to yield a semi-crystalline residue. This residue is chromatographed over neutral alumina (Woelm ®, Grade IV) to yield the 25-alcohol of the title. The compound is then crystallized from methanol, M.P. 133°–135° C.

EXAMPLE 10

Analogues of the above compound wherein R is ethyl, propyl, tert butyl, isohexyl, are readily prepared wherein R$^1$ is hydrogen and R$^2$ and R$^3$ are methyl, R$^1$ is methyl and R$^2$ and R$^3$ are hydrogen, R$^1$ and R$^2$ are hydrogen and R$^3$ is methyl.

I claim:

1. A compound of the formula

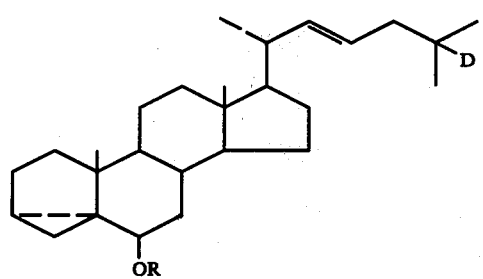

wherein R is alkyl of one to six carbon atoms, inclusive, and D is selected from the group consisting of O− and

wherein R$^4$ is selected from the group consisting of alkyl of one to six carbon atoms, inclusive, phenyl, benzyl and phenethyl.

2. A compound of the formula

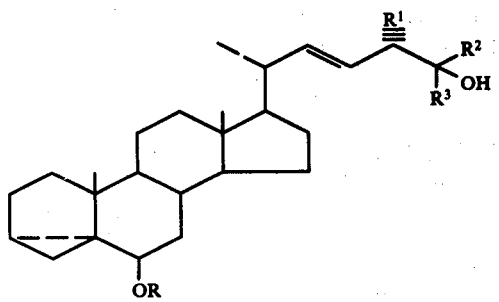
wherein R is alkyl of one to six carbon atoms, inclusive and $R^1$, $R^2$ and $R^3$ are the same or different and are hydrogen or methyl.
3. A compound in accordance with claim 2 wherein $R^1$ is hydrogen and $R^2$ and $R^3$ are methyl.
4. A compound in accordance with claim 3 wherein R is methyl.
* * * * *